US012778913B2

(12) United States Patent
Wall

(10) Patent No.: US 12,778,913 B2
(45) Date of Patent: Nov. 3, 2026

(54) TREATMENT OF AGE-RELATED MACULAR DEGENERATION, GLAUCOMA, AND DIABETIC RETINOPATHY WITH N-ACETYLCYSTEINE AMIDE (NACA) OR (2R,2R')-3,3'-DISULFANEDIYL BIS(2-ACETAMIDOPROPANAMIDE)(DiNACA)

(71) Applicant: Nacuity Pharmaceuticals, Inc., Fort Worth, TX (US)

(72) Inventor: G. Michael Wall, Fort Worth, TX (US)

(73) Assignee: Nacuity Pharmaceuticals, Inc., Fort Worth, TX (US)

( * ) Notice: Subject to any disclaimer, the term of this patent is extended or adjusted under 35 U.S.C. 154(b) by 332 days.

(21) Appl. No.: 18/447,720

(22) Filed: Aug. 10, 2023

(65) Prior Publication Data

US 2023/0381120 A1 Nov. 30, 2023

Related U.S. Application Data

(63) Continuation-in-part of application No. 16/738,819, filed on Jan. 9, 2020, now Pat. No. 11,766,413.

(60) Provisional application No. 62/791,396, filed on Jan. 11, 2019.

(51) Int. Cl.

| | |
|---|---|
| ***A61K 31/16*** | (2006.01) |
| ***A61K 31/047*** | (2006.01) |
| ***A61K 31/085*** | (2006.01) |
| ***A61K 31/194*** | (2006.01) |
| ***A61K 31/198*** | (2006.01) |
| ***A61K 31/235*** | (2006.01) |
| ***A61K 31/355*** | (2006.01) |
| ***A61K 31/375*** | (2006.01) |
| ***A61K 31/685*** | (2006.01) |
| ***A61K 33/42*** | (2006.01) |

(52) U.S. Cl.

CPC ............ *A61K 31/16* (2013.01); *A61K 31/047* (2013.01); *A61K 31/085* (2013.01); *A61K 31/194* (2013.01); *A61K 31/198* (2013.01); *A61K 31/235* (2013.01); *A61K 31/355* (2013.01); *A61K 31/375* (2013.01); *A61K 31/685* (2013.01); *A61K 33/42* (2013.01)

(58) Field of Classification Search

CPC ...................................................... A61K 31/16

See application file for complete search history.

(56) References Cited

U.S. PATENT DOCUMENTS

| | | | |
|---|---|---|---|
| 1,114,369 | A | 10/1914 | Kukla |
| 3,340,147 | A | 9/1967 | Alexander |
| 5,874,468 | A | 2/1999 | Atlas |
| 6,420,429 | B1 | 7/2002 | Atlas |
| 8,354,449 | B2 | 1/2013 | Goldstein |
| 8,937,099 | B2 | 1/2015 | Goldstein |
| 8,993,627 | B2 | 3/2015 | Goldstein |
| 9,216,162 | B2 | 12/2015 | Goldstein |
| 9,763,902 | B2 | 9/2017 | Warner |
| 9,889,103 | B2 | 2/2018 | Warner |
| 10,869,846 | B2 | 12/2020 | Goldstein |
| 11,052,018 | B2 | 7/2021 | Molnar |
| 11,092,017 | B2 | 8/2021 | Propheter-Hinckley |
| 2003/0027745 | A1 | 2/2003 | Repine |
| 2005/0112572 | A1 | 5/2005 | Pincemail |
| 2009/0234011 | A1 | 9/2009 | Goldstein |
| 2012/0142550 | A1 | 6/2012 | Zehnder |
| 2012/0150029 | A1 | 6/2012 | Debuc |
| 2013/0303436 | A1 | 11/2013 | Wilson |
| 2015/0164830 | A1 | 6/2015 | Goldstein |
| 2017/0020914 | A1 | 1/2017 | Castro Feo |
| 2017/0333375 | A1 | 11/2017 | Campochiaro |
| 2017/0370945 | A1 | 12/2017 | Campochiaro |
| 2019/0135741 | A1 | 5/2019 | Wall |
| 2020/0281944 | A1 | 9/2020 | Piraee |
| 2021/0228509 | A1 | 7/2021 | Wall |

FOREIGN PATENT DOCUMENTS

| | | | |
|---|---|---|---|
| CA | 3078680 | A1 | 5/2019 |
| CA | 3079196 | C | 5/2021 |
| CN | 108618993 | A | 10/2018 |
| EP | 1975621 | A4 | 2/2009 |
| GB | 1114369 | A | 5/1968 |
| JP | 2005350405 | A | 12/2005 |
| JP | 2008538586 | A5 | 7/2009 |
| JP | 2013533234 | A | 8/2013 |
| JP | 202023549 | A | 2/2020 |
| WO | 2003016527 | A3 | 12/2003 |
| WO | 2004012652 | | 4/2004 |
| WO | 2004028536 | A1 | 4/2004 |

(Continued)

OTHER PUBLICATIONS

Dong et al., Onv. Opthalmology & Visual Science, 55(16) (2014).*

Adil, et al. "N-acetylcysteine in dermatology" Indian Journal of Dermatology, Feb. 2018.

Australian Patent Office (ISA), International Search Report and Written Opinion for PCT/US2015/060172 Dated Apr. 13, 2016, 12 pg.

Australian Patent Office (ISA), International Search Report and Written Opinion for PCT/US2018/052065 dated Jan. 10, 2019, 10 pg.

Australian Patent Office, International Search Report and Written Opinion PCT/US2021/036210 dated Jul. 19, 2021, 12 pp.

(Continued)

*Primary Examiner* — Paul V Ward

(74) *Attorney, Agent, or Firm* — Edwin S. Flores; Daniel J. Chalker; Chalker Flores, LLP

(57) ABSTRACT

The present invention includes a method for the treatment of age-related macular degeneration, glaucoma, or diabetic retinopathy in a human that comprises administering to the human a therapeutically effective amount of N-acetylcysteine amide (NACA) or (2R,2R')-3,3'-disulfanediyl bis(2-acetamidopropanamide) (diNACA) sufficient to treat or reduce the symptoms of the age-related macular degeneration, glaucoma, or diabetic retinopathy.

11 Claims, 3 Drawing Sheets

(56) References Cited

FOREIGN PATENT DOCUMENTS

| | | | | |
|---|---|---|---|---|
| WO | 2006116353 | A2 | 11/2006 | |
| WO | 2010048716 | A1 | 5/2010 | |
| WO | 2011044230 | A2 | 4/2011 | |
| WO | WO2013/163545 | * | 4/2013 | ........... A61K 31/195 |
| WO | 2013138744 | A1 | 9/2013 | |
| WO | 2013163545 | A1 | 10/2013 | |
| WO | 2014025792 | A1 | 2/2014 | |
| WO | 2014100361 | A1 | 6/2014 | |
| WO | 2015148880 | | 10/2015 | |
| WO | 2016073931 | A1 | 5/2016 | |
| WO | 2016073829 | A9 | 6/2016 | |
| WO | 2017161318 | A1 | 9/2017 | |
| WO | 2019060623 | A1 | 3/2019 | |
| WO | 2019060634 | A1 | 3/2019 | |
| WO | 2019060704 | A1 | 3/2019 | |
| WO | 2019094383 | A1 | 5/2019 | |
| WO | 2019097434 | A1 | 5/2019 | |
| WO | 2019103915 | A1 | 5/2019 | |
| WO | 2020102810 | A1 | 5/2020 | |
| WO | 2020146660 | A1 | 7/2020 | |
| WO | 2020146666 | A1 | 7/2020 | |
| WO | 2020146674 | A1 | 7/2020 | |

OTHER PUBLICATIONS

Australian Patent Office, Examination Report for Australian Appl. No. 2020227015 dated Sep. 24, 2021, 6 pp.

Canadian Patent Office, Examination Report for Appl. No. 3,046,363 dated Jun. 6, 2022, 4 pp.

Campochiaro, et al. "Is there Excess Oxidative Stress and Damage in Eyes of Patients with Retinitis Pigmentosa?" Antioxidants & Redox Signaling, (2015) 23(7):643-648.

Campochiaro, et al. "The Mechanism of Cone Cell Death in Retinitis Pigmentosa", Progress in Retinal and Eye Research (2018), 62:24-37.

Demirel, et al. "The preventive effect of N-acetylcysteine on radiation-induced dermatitis in a rat model" Journal of BUON, 15:577-582, 2010.

European Patent Office, Extended European Search Report for 15770142.6 dated Oct. 20, 2017.

European Patent Office, Extended European Search Report for 15858590.1 dated May 2, 2018.

European Patent Office, Extended European Search Report for EP 20738980.0 dated Jan. 28, 2022, 9 pp.

Eye & Health—No. 25, Eye & Health, Special Topic: Drug therapy of human eye disease, Planning and production by Soshinsha, Co., Ltd., 2012, p. 1-7, <URL>https://www.skk-net.com/health/me/files/Eye25_1902_2.pdf.

Hong, et al. "Effect of High-Dose Intravenous N-acetylcysteine on the Concentration of Plasma Sulfur-Containing Amino Acids", The Korean Journal of Internal Medicine: 20:217-223, 2005.

Hsu, et al. "Feasibility of corneal drug delivery of cysteamine using vitamin E modified silicone hydrogel contact lenses" European Journal of Pharn1aceutics and Biopharn1aceutics 85 (2013) 531-540.

Intellectual Property India, First Examination Report for Indian Appl. No. 201917036550 dated Sep. 22, 2021, 7 pp.

Levine, R.L., "Carbonyl modified proteins in cellular regulation, aging, and disease" Free Radic Biol Med, 2002. 32(9): p. 790-6.

Li, et al, "A Convenient Synthesis of Amino Acid Methyl Esters", Molecules (2008), 13:1111-1119.

Martinez-Fernandez De La Camara, et al., Altered Antioxidant-Oxidant Status in Aqueous Humor and Peripheral Blood of Patents with Retinitis Pigmentosa, PLOS One (2013), 8(9):E74223.

Minozzi, et al., "An Insight into the Radical Thiol/Yne Coupling: The Emergence of Arylalkyne-tagged Suggars for te Direct Photoinduced Glycosylation of Cysteine Containing Peptides", J. Org. Chem, 2011, 76, 450-459.

Offen, et al. "A low molecular weight copper chelator crosses the blood-brain barrier and attentuates experimental autoimmune encephalomyelitis" Journal of Neurochemistry, 2004, 89, 1241-1251.

Reagan-Shaw, et al. "Dose translation from animal to human studies revised" The FASEB Journal, Mar. 2007, vol. 22, (659-661).

Riley, et al., "Glutathione in the aqueous humor of human and other species." Investigative ophthalmology & visual science, (1980), 9(1):94-96.

Rubin BK. "Aerosol Medications for Treatment of Mucus Clearance Disorders Respiratory care" 2015; 60(6): 825-832.

Shams, et al. "Treatment of corneal cystine crystal accumulation in patients with cystinosis" Clinical Opthamalogy, Oct. 10, 2014, 2077-2078.

Shen, et al., "Oxidative damage in age-related macular degeneration," Histology and Histopathology (2007), 22 (12):1301-1308.

Sunitha, et al. "N-Acetylcysteine amide: a derivative to fulfill the promises of N-Aceylcysteine" Free Radical Resarch, May 2013, 47(5), 357-367.

Supelco "Methanolic H2S04 (10./o v/v)" 1997, Sigma-Aldrich Co., 2 Pages.

Tsai, et al. "Topical TV-Acetylcysteine Accelerates Wound Healing in Vitro and in Vivo via the PKC/Stat3 Pathway" Int. J. Mol. Sci., 2014, 15, 7563-7578.

University of Sao Paulo, et al. "N-Acetyl Cysteine for Cystinosis Patients", ClinicalTrials.gov [online], identifier: NCT01614431, Last update posted: Jun. 20, 2012, htps://clinicaltrials.gov/ct2/show/NCT01614431, [retrieved online Jul. 9, 2021].

Usui, et al., "Overexpression of SOD in retina: Need for increase in H202-detoxifying enzyme in same cellular compartment," Free Radical Biology and Medicine (2011 ), 51(7):1347-1354.

Vaisbich, et al. "Oxidative Stress in Cystinosis Patients" Nephron Extra, 2011; 1:73-77, publishes online Sep. 19, 2011.

Kunisada, et al. "CXCL1 Inhibition Regulates UVB-Induced Skin Inflammation and Tumorigenesis in Xpa-Deficient Mice" Journal of Investigative Dermatology (2017), 137, 1975-1983.

Elmonem, et al. "Cystinosis: a review" Orphanet Journal of Rare Diseases (2016) 11:47.

European Office Action, Examination Report for EP Patent Appl No. 21217485.8 Dated Nov. 20, 2023, 5 pp.

European Patent Office, Extended European Search Report for EP 20738196.3 dated Sep. 22, 2022, 12 pp.

Grinberg, et al., "N-acetylcysteine amide, a novel cell-permeating thiol, restores cellular glutathione and protects human red blood cells from oxidative stress," Free Radical Biol Med. (2005) ;38(1):136-145.

Isokawa, et al., Analytical methods involving separation techniques for determination of low-molecular-weight biothiols in human plasma and blood. J Chrom B, 964 (2014) 103-115.

Japan Patent Office, Notification of Reasons for Refusal dated Dec. 18, 2023 for Japanese Appl. No. 2021-540019 (with english translation), 8 pp.

Jastrzbska, et al., "N-acetylcysteine amide (AD4) reduces cocaine-induced reinstatement." Psychopharmacology 2016;33:3437-3448.

Jones, "Extracellular Redox State: Refining the Definition of Oxidative Stress in Aging," Rejuvenation Research (2006), 9(2):169-181.

Kahns, et al., "Prodrugs as drug delivery systems. 107. Synthesis and chemical and enzymatic hydrolysis kinetics of various mono-and diester prodrug of N-acetylcysteine." Int J Pharm (1990), 62:193-205.

Katz, et al., Cerebrospinal fluid concentrations of N-acetylcysteine after oral administration in Parkinson's disease. Parkinsonism and Related Disorders, 21 (2015) 500-503.

Kelly, "Clinical applications of N-acetylcysteine." Altern Med Rev J Clin Ther. (1998), 3(2):114-27.

Kim, et al., "N-Acetylcysteine increases corneal cell survival in a mouse model of Fuchs endothelial corneal dystrophy," Experimental Eye Research (2014), 127:20-25.

Komeima, et al., "Antioxidants reduce cone cell death in a model of retinitis pigmentosa." PNAS, (2006), 103 (30):11300-11305.

Komeina, et al., "Antioxidants slow photoreceptor cell death in mouse models of retinitis pigmentosa." J Cell Physiol. (2007), 213(3):809-15.

(56) References Cited

OTHER PUBLICATIONS

Komeina, et al., "Blockade of neuronal nitric oxide synthase reduces cone cell death in a model of retinitis pigmentosa." Free Radic Biol Med, (2008), 45(6):905-12.
Kusmierek, et al., Ultraviolet derivatization of low-molecular-mass thiols for high performance liquid chromatography and capillary electrophoresis analysis, J Chrom B, 879 (2011) 1290-1307.
Lee, et al., "N-Acetylcysteine Promotes Long-Term Survival of Cones in a Model of Retinitis Pigmentosa," J Cell Physiol (2011), 226:1843-1849, published online Nov. 10, 2010.
Liu, et al., "A rabbit model to study biochemical damage to the lens after vitrectomy: effects of N-acetylcysteine." Exp Eye Res. 2009;88(6):1165-70.
Lu, et al., "Effects of Different Types of Oxidative Stress in RPE Cells," J Cell Phys (2006), 206(1):119-125.
Maddirala, et al. "Prevention and reversal of selenite-induced cataracts by N-acetylcysteine amide in Wistar rats" BMC Ophthalmology (2017) 17:54.
Maeda, et al., "Important Role of the 3-Mercaptopropionamide Moiety in Glutathione: Promoting Effect on Decomposition of the Adduct of Glutathione with the Oxoammonium Ion of TEMPO", J Organic Chem (2005). 70:8338-8343.
Martin, Tellis, "Amides of N-Acylcysteines as Mucolytic Agents", J Med Chem (1967), 10:1172-1176.
McMenamim, et al., Simultaneous analysis of multiple aminothiols in human plasma by high performance liquid chromatography with fluorescence detection, J Chrom B, 877 (2009) 3274-3281.
Miller, WF. "Aerosol therapy in acute and chronic respiratory disease." Arch Intern Med 1973;131:148-155.
Monostori, et al., Determination of glutathione and glutathione disulfide in biological samples: an in-depth review. J Chrom B, 877 (2009) 3331-3346.
Moore, et al., A new LC-MS/MS method for the clinical determination of reduced and oxidized glutathione from whole blood. J Chrom B, 929 (2013) 51-55.
Nakagami, et al. "A novel Nrf2 activator from microbial transformation inhibits radiation-induced dermatitis in mice," Journal of Radiation Research, vol. 57, No. 5, 2016, pp. 567-571.
Nash, et al., "Nebulized and oral thiol derivatives for pulmonary disease in cystic fibrosis." Cochrane Database Syst Rev 2009;(1):CD007168.
New, et al., Evaluation of BEH C18, BEH HILIC, and HSS T3 (C18) Column Chemistries for the UPLC-MS-MS Analysis of Glutathione, Glutathione Disulfide, and Ophthalmic Acid in Mouse Liver and Human Plasma. J Chrom Sci, 46 (2008) 209-214.
Niemeyer, Selective Rod-and Cone-ERG Responses on Retinal Degenerations, Digital Journal of Ophthalmology, 1998, vol. 4, No. 10, 1998.
Nozal, et al., Determination of glutathione, cysteine, and N-acetylcysteine in rabbit eye tissues using high-performance liquid chromatography and post-column derivatization with 5,5'-dithiobis(2-nitrobenzoic acid). J Chrom A, 778 (1997) 347-353.
Park, et al.: "Targeted and Reversible Blood-Retinal Barrier Disruption via Focused Ultrasound and Microbubbles" PLoS One (2012), 7(8):e42754.
Poole, et al., "Mucolytic agents versus placebo for chronic bronchitis or chronic obstructive pulmonary disease." Cochrane Database Syst Rev 2015;(7):CD001287).
Reyes, et al., Neuronal glutathione content and antioxidant capacity can be normalized in situ by N-acetyl cysteine concentrations attained in human cerebrospinal fluid, Neurotherapeutics, 13 (2016) 217-225.
Šalamon, et al., "Medical and Dietary Uses of N-Acetylcysteine." Antioxidants 2019, 8, 111.
Schimel, et al., "N-Acetylcysteine Amide (NACA) Prevents Retinal Degeneration by Up-Regulating Reduced Glutathione Production and Reversing Lipid Peroxidation." The American Journal of Pathology, (2011), 178 (5):2032-2043.
Sekhon, "Exploiting the Poer of Stereochemistry in Drugs . . . ", Journal of Modern Medicinal Chemistry, 2013, 10-36.
Shen, et al., "Oxidative damage is a potential cause of cone cell death in retinitis pigmentosa." J Cell Physiol, (2005), 203(3):457-64.
Shintani, et al., "Review and Update: Current treatment trends for Patients with Retinitis Pigmentosa," Optometry (2009), 80:384-401.
Squellerio, et al., Direct glutathione quantification in human blood by LC-MS/MS: comparison with HPLC with electrochemical detection. J Pharm Biomed Anal, 71 (2012) 111-8.
Stey, et al., "The effect of oral N-acetylcysteine in chronic bronchitis: a quantitative systematic review." Eur Respir J. 2000; 16(2):253-62.
Suh, et al., Clinical assay of four thiol amino acid redox couples by LC-MS/MS: utility in thalassemia, J Chrom B, 877 (2009) 3418-3427.
Sunitha, et al., N-acetylcysteine amide: a derivative to fulfull the promises of N-acetylcysteine. Free Radic Res, 47 (2013) 357-367.
Tam, et al., "Nebulized and oral thiol derivatives for pulmonary disease in cystic fibrosis." Cochrane Database Syst Rev 2013;(7):CD007168.
Tarrant et al. "Mucoactive agents for adults with acute lung conditions: A systematic review." Heart & Lung (2019) 48 (2):141-147.
Tobwala et al. "N-acetylcysteine Amide (NACA), a Novel GSH Prodrug: Its Metabolism and Implications in Health", Labrou, 2013, Capter VI. ISBN:978-1-62417-460-5.
Tse, et al., "High-dose N-acetylcysteinine in stable COPD: the 1-year, double-blind, randomized, placebo-controlled HIACE study." Chest, (2013). 144(1):106-118.
Tuson, et al., "Overexpression of CERKL, a gene responsible for retinitis pigmentosa in humans, protects cells from apoptosis induced by oxidative stress." Mol Vis. (2009), 15:168-80.
United States Patent & Trademark Office (ISA) International Search Report and Written Opinion PCT/US2015/059589 Dated Feb. 2, 2016, 10 pg.
Amer, et al., "N-acetylcysteine amide (AD4) attenuates oxidative stress in beta-thalassemia blood cells." Biochimica et Biophysica Acta 1780 (2008) 249-255.
Ates, et al., "Antioxidant and free radical scavenging properties of N-acetylcysteine amide (NACA) and comparison with N-acetylcysteine (NAC)." Free Radic Res. (2008), 42(4):372-7.
Australian Patent Office (ISA), International Search Report and Written Opinion for PCT/US2018/059446 dated Dec. 31, 2018, 15 pg.
Australian Patent Office (ISA), International Search Report and Written Opinion for PCT/US2018/061357 dated Dec. 18, 2018, 11 pg.
Australian Patent Office (ISA), International Search Report and Written Opinion for PCT/US2020/012968 dated Mar. 13, 2020, 10 pp.
Australian Patent Office (ISA), International Search Report and Written Opinion for PCT/US2020/012975 dated Mar. 13, 2020, 12 pp.
Australian Patent Office (ISA), International Search Report and Written Opinion for PCT/US2020/012983 dated Mar. 13, 2020, 15 pp.
Australian Patent Office, International Search Report and Written Opinion PCT/US2021/014819 dated Mar. 25, 2021, 18 pp.
Babizhayev, et al., Revival of the Lens Transparency with N-Acetylcarnosine.: Current Drug Therapy, 2006:1; 91-116.
Bahat-Stroomza, et al., A novel thiol antioxidant that crosses the blood brain barrier protects dopaminergic neurons in experimental models of Parkinson's disease. European Journal of Neuroscience, 2005; 21: 637-646.
Banerjee, et al., "HIV proteins (gp120 and Tat) and methamphetamine in oxidative stress-induced damage in the brain: Potential role of the thiol antioxidant N-acetylcysteine amide." Free Radic Biol Med. May 15, 2010; 48(10): 1388-1398.
Bean, et al., "Comparative evaluation of antioxidant reactivity within obstructed and control rabbit urinary bladder tissue using FRAP and CUPRAC assays," Molecular and Cellular Biochemistry (2008) 323(1-2):139-142.
Bernardes, et al., "From Disulfide- to Thioether-Linked Glycoproteins" Angewandte Chemie, Supporting Information (2008), S1-S97.

(56) References Cited

OTHER PUBLICATIONS

Betteridge, John What is Oxidative Stress Metabolism, vol. 49, No. 2, Feb. 2000, pp. 3-8.
Boone, Kevin "The K-Zone: Biophysical Data Tables", 1994-2006, downloaded from www.kevinboone.com on Mar. 14, 2009.
Buss, et al., "Protein carbonyl measurement by a sensitive ELISA method." Free Radic Biol Med, (1997), 23(3):361-6.
Campochiaro, et al., "Oral N-acetylcysteine improves cone function in retinitis pigmentosa patients in phase I trial." J Clin Invest. 2020 130(3):1527-1541.
Carey, et al., "In vivo inhibition of I-buthionine-(S, R)-sulfoximine-induced cataracts by a novel antioxidant, N-acetylcysteine amide." Free Radical Biol Med. 2011;15.
Carey, et al. "N-acetyl-L-cysteine amide protects retinal pigment epithelium against methamphetamine-induced oxidative stress" Journal of Biophysical Chemistry, vol. 3, No. 2, 101-110 (2012).
Carroll, et al., "Simultaneous quantitation of oxidized and reduced glutathione via LC-MS/MS: An insight into the redox state of hematopoietic stem cells." Free Radical Biology and Medicine, 97 (2016) 85-94.
Celma, et al., "Determination of N-acetylcysteine in human plasma by liquid chromatography coupled to tandem mass spectrometry." J Chrom A, 870 (2000) 13-22.
Chastain, et al. "Distribution of topical ocular nepafenac and its active metabolite amfenac to the posterior segment of the eye." Exp Eye Res (2016), 145:58-67.
Davies, et al., "Measurements of protein carbonyls, ortho- and meta-tyrosine and oxidative phosphorylation complex activity in mitochondria from young and old rats." Free Radic Biol Med, (2001), 31(2):181-90.
Devries, et al. "N-acetyl-l-cysteine." J Cell Biochem Suppl (1993), 17F:270-277.
Dietz, et al., "Photochemical Reduction of 5-Bromouracil by Cysteine Derivatives and Coupling of 5-Bromouracil to Cystine Derivatives," Photochemistry and Photobiology (1989), 49(2):121-129.
Dietzsch, et al., "Cystic fibrosis: comparison of two mucolytic drugs for inhalation treatment (acetylcysteine and arginine hydrochloride)." Pediatrics 1975;55:96-100.
Dong, et al., "Compared with N-acetylcysteine (NAC), N-Acetylcysteine Amid (NACA) Provides Increased Protein of Cone Function in a Model of Retinitis Pigmentosa." Investigative Ophthalmology Visual Science, (2014), 55:1-2. (Abstract).
Ehre, et al. An Improved Inhaled Mucolytic to Treat Airway Muco-obstructive Diseases. Am J Respir Crit Care Med. Jan. 15, 2019;199(2):171-180. doi: 10.1164/rccm.201802-0245OC.
Ercal, et al., "Effects of a thiol antioxidant in various cataract models," Acta Ophthalmologica (2016), 94:S256 (Abstract).
Ercal, et al., High-performance liquid chromatography assay for N-acetylcysteine in biological samples following derivatization with N-(1-pyrenyl)maleimide. J Chrom B, 685 (1996) 329-334.
European Patent Office, Extended European Search Report for EP 15857309.7 dated May 23, 2018.
European Patent Office, Extended European Search Report for EP 18876329.6 dated Oct. 29, 2019.
European Patent Office, Extended European Search Report for EP 18882212.6 dated Jul. 6, 2021, 8 pp.
Giustarini, et al., Pitfalls in the analysis of the physiological antioxidant glutathione (GSH) and its disulfide (GSSG) in biological samples: an elephant in the room. J Chrom B., 1019 (2016) 21-28.
Han, et al., "Efficacy of nebulized acetylcysteine for relieving symptoms and reducing usage of expectorants in patients with radiation pneumonitis." Thoracic Cancer 2018; 1-6. doi: 10.1111/1759-7714.12938.
Heymann, et al., "The preparation and Some Biological Properties of the Asperagine Analog L-2@-Amino-2-carboxyethanesulfonamide," J Am Chem Soc (1959), 81(19):5125-5128.
Usui, et al., "NADPH oxidase plays a central role in cone cell death in retinitis pigmentosa." J Neurochem. (2009), 110 (3):1028-37.
Wang, et al., "Hyperoxia-induced lens damage in rabbit: protective effects of N-acetylcysteine." Mol Vis. 2009;15:2945-52.
Wang, et al., "Relationship of protein-glutathione mixed disulfide and thioltransferase in H2O2-induced cataract in cultured pig lens." Exp Eye Res. May 1997;64(5):693-700.
Watanabe, et al., "Skin-whitening and skin-condition-improving effects of topical oxidized glutathione: a double-blind and placebo-controlled clinical trial." Clin Cosmetic Inv Dermatol. 2014;7:267-274.
Weng, Bioanalytical liquid chromatography tandem mass spectrometry methods on underivatized silica columns with aqueous/organic mobile phases. J Chrom B, 796 (2003) 209-224.
Wu, et al., "Effects of N-acetylcysteine amide (NACA, a thiol antioxidant on radiation-induced cytotoxicity in Chenese hamster ovary cells," Life Sciences (2008), 82:1122-1130.
Wu, et al., Separation and quantification of N-acetyl-L-cysteine and N-acetyl-cysteine-amide by HPLC with fluorescence detection. Biomed Chromatogr, 20 (2006) 415-422.
Yu, et al., "Intraretinal oxygen levels before and after photoreceptor loss in the RCS rat." Invest Ophthalmol Vis Sci, (2000), 41(12):3999-4006.
Zhang, et al., "Effects of N-acetylcysteine and glutathione ethyl ester drops on streptozotocin-induced diabetic cataract in rats." Mol Vis. 2008;14:862-70.
Usui, et al., "Increased expression of catalase and superoxide dismutase 2 reduces cone cell death in retinitis pigmentosa." Mol Ther J Am Soc Gene Ther. (2009), 17(5):778-86.

* cited by examiner

TREATMENT OF AGE-RELATED MACULAR DEGENERATION, GLAUCOMA, AND DIABETIC RETINOPATHY WITH N-ACETYLCYSTEINE AMIDE (NACA) OR (2R,2R')-3,3'-DISULFANEDIYL BIS(2-ACETAMIDOPROPANAMIDE)(DiNACA)

CROSS-REFERENCE TO RELATED APPLICATIONS

This application claims priority to U.S. Provisional Application Ser. No. 62/791,396, filed Jan. 11, 2019, and is a continuation-in-part of U.S. application Ser. No. 16/738,819, filed Jan. 9, 2020, the entire contents of each of which are incorporated herein by reference.

STATEMENT OF FEDERALLY FUNDED RESEARCH

Not applicable.

TECHNICAL FIELD OF THE INVENTION

The present invention relates in general to the field of compositions and methods for treating age-related macular degeneration, glaucoma, and/or diabetic retinopathy using N-acetylcysteine amide (NACA) or (2R,2R')-3,3'-disulfanediyl bis(2-acetamidopropanamide) (diNACA) as prodrugs to NAC.

BACKGROUND OF THE INVENTION

Age-related macular degeneration (AMD) is the term used for describing lost or blurred vision in the center of the visual field. A difficulty with detecting early stages of AMD is the lack of symptoms, which are very gradual and may affect one or both eyes. While all vision may not be lost, the loss of vision in the center of the visual field makes it difficult to recognize objects, drive, read, or perform normal activities. Typically, AMD is a disease that affects individuals later in life, and is made worse by smoking, hypertension, atherosclerosis, elevated cholesterol, obesity, fat intake, and exposure to sunlight. There are also genetic components to AMD, as sibling studies have shown an increase in recurrence ratios, and, to date, at least 5 different genes have shown some linkage to AMD. Unfortunately, AMD is a complex disease that results from a variety of environmental, genetic, and lifestyle factors.

Clinical signs of AMD include a distortion in the visual field, which typically takes the form of metamorphopsia, which is a type of vision distortion in which a grid of straight lines appears wavy and parts of the grid may appear blank. Other symptoms of AMD include: slow recovery of visual function as a result of exposure to bright light (e.g., using a photostress test), a drastic decrease in visual acuity, blurred vision, trouble discerning colors, and a loss of contrast sensitivity. AMD shows a processor accumulation of drusen deposits in the macula, between the retinal pigment epithelium, and the underlying choroid. These drusen are the build-up of extracellular proteins and lipids that are believed to damage the retina over time. However, the presence of drusen is not indicative of disease progression, as the majority of people over age 60 have drusen without any negative effects. Various stages of AMD are known, and are generally divided into early AMD, intermediate AMD, late AMD, Dry (or nonexudative) AMD, atrophic (or geographic) AMD, and/or wet (or exudative) AMD.

Currently, there is no approved therapy that stops the evolution of the disease or restores vision. To date, the therapeutic approach is restricted to slowing down the degenerative process by the use of vitamin and mineral supplements, however, no significant effect was found from the use of these agents.

As such, there still exists a need for novel compositions and methods for treatment of age-related macular degeneration.

Diabetic retinopathy (DR) is a leading cause of blindness globally and its pathogenesis has still not been completely elucidated. Some studies show a close relation between oxidative stress. Zhu et al conducted a study aimed to investigate the effects of anti-oxidant in DR and expression of vascular endothelial growth factor (VEGF) and intercellular adhesion molecule-1 (ICAM-1) from retinal blood vessels in diabetic rats. (Zhu et al. Effect of antioxidant N-acetylcysteine on diabetic retinopathy and expression of VEGF and ICAM-1 from retinal blood vessels of diabetic rats. Molecular Biol Rep 2012; 39(4): 3727-3735.) Diabetic rat models were established by intraperitoneal injection of streptozotocin (60 mg/kg) and confirmation of high serum glucose levels in the animals. Antioxidant N-acetylcysteine was given to diabetic rats to elicit antioxidative responses, and rats were sacrificed at 3 and 5 months. Ultrastructures of retinal vascular tissues were observed under transmission electron microscope, and pathology of retinal capillaries was examined using retinal vascular digest preparations. Changes in the expression of VEGF and ICAM-1 were examined by immunofluorescence; and reactive oxygen species contents in the retinas were detected using dichlorofluorescein assay. Compared with normal rats, diabetic rats displayed significant retinopathy both under electronic and light microscopy, accompanied by elevated reactive oxygen species contents in the retinas; N-acetylcysteine treatment alleviated the pathological changes and also decreased reactive oxygen species, most significantly at 5 months. VEGF and ICAM-1 expressions were significantly up-regulated in retinal blood vessels from diabetic rats, and such up-regulation was attenuated by N-acetylcysteine treatment. The expression of both factors returned to basal levels after 5-month treatment with N-acetylcysteine. Long-term N-acetylcysteine treatment exerts protective effects on the diabetic retinas, possibly through its down-regulation of the expression of VEGF and ICAM-1, and reduction of reactive oxygen species content in retinal vascular tissues in diabetic rats. (Zhu et al. 2012).

SUMMARY OF THE INVENTION

In accordance with an embodiment, the present invention provides a method for the treatment of age-related macular degeneration, glaucoma, and/or diabetic retinopathy in an animal or human that comprises administering to the animal or human a therapeutically effective amount of N-acetylcysteine amide (NACA). In one aspect, the NACA is provided in or with a pharmaceutically acceptable carrier. In another aspect, the NACA is administered intraocularly, subretinally, intravitreally, orally, intravenously, intramuscularly, topically, sublingually, or rectally. In a other aspect, the NACA is administered in daily doses of about 0.5, 1, 2, 3, 4, 5, 6, 7, 8, 9, 1, 15, 20, 25, 30, 40, 50, 60, 70, 75, 80, 90, 100, 110, 120, 125, 130, 140 or 150 mg/Kg. In another aspect, NACA is administered two or three times daily. In another aspect, NACA is administered with a second active agent selected from at least one of ascorbic acid, cysteine hydrochloride, sodium bisulfate, sodium metabisulfite, sodium sulfite, ascorbyl palmitate, butylated hydroxyanisole (BHA), butylated hydroxytouene (BHT), lecithin, propyl gallate, α-tocopherol, citric acid, ethylenediamine tetraacetic acid (EDTA), sorbitol, tartaric acid, or phosphoric acid. In another aspect, the dose for administration is 100, 150, 150, 300, 333, 400, 500, 600, 700, 750, 800, 900, 1,000, 2,500, 5,000, 7,500, or 10,000 mg per dose. In another aspect, the does for administration is 0.1-0.25, 0.1-0.4, 0.35-0.5, 0.5-1, 1-2, 1-3, 1-4, 1-5, 1-2.5, 2.5-3.5, 4-6, 5-8, 6-9, 7-10 grams per dose. In another aspect, the NACA is delivered orally via a mini-tablet, capsule, tablet, effervescent, dual release, mixed release, sachet, powder, or liquid. In another aspect, the NACA is administered prophylactically to prevent age-related macular degeneration, glaucoma, and/or diabetic retinopathy. In another aspect, the animal is a human. In another aspect, the dose for administration is between 100 and 900 micrograms per dose. In another aspect, the dose for administration is 100, 150, 150, 300, 350, 400, 500, 600, 700, 750, 800, 900, 1,000, 2,500, 5,000, 7,500, or 10,000 micrograms per dose. In another aspect, the diNACA is administered as an implant one, two, or three times per year.

In accordance with another embodiment, the present invention includes a method for the treatment of age-related macular degeneration, glaucoma, and/or diabetic retinopathy comprising: identifying a human in need of treatment for age-related macular degeneration, glaucoma, and/or diabetic retinopathy; and administering to the human a therapeutically effective amount of N-acetylcysteine amide (NACA) sufficient to treat age-related macular degeneration, glaucoma, and/or diabetic retinopathy. In one aspect, the NACA is provided in or with a pharmaceutically acceptable carrier. In another aspect, the NACA is administered intraocularly, subretinally, intravitreally, orally, intravenously, intramuscularly, topically, sublingually, or rectally. In another aspect, the NACA is administered in daily doses of about 0.5, 1, 2, 3, 4, 5, 6, 7, 8, 9, 10, 15, 20, 25, 30, 40, 50, 60, 70, 75, 80, 90, 100, 110, 120, 125, 130, 140 or 150 mg/Kg. In another aspect, NACA is administered two or three times daily. In another aspect, NACA is administered with a second active agent selected from at least one of ascorbic acid, cysteine hydrochloride, sodium bisulfate, sodium metabisulfite, sodium sulfite, ascorbyl palmitate, butylated hydroxyanisole (BHA), butylated hydroxytouene (BHT), lecithin, propyl gallate, α-tocopherol, citric acid, ethylenediamine tetraacetic acid (EDTA), sorbitol, tartaric acid, or phosphoric acid. In another aspect, the dose for administration is 100, 150, 150, 300, 333, 400, 500, 600, 700, 750, 800, 900, 1,000, 2,500, 5,000, 7,500, or 10,000 mg per dose. In another aspect, the dose for administration is 0.1-0.25, 0.1-0.4, 0.35-0.5, 0.5-1, 1-2, 1-3, 1-4, 1-5, 1-2.5, 2.5-3.5, 4-6, 5-8, 6-9, 7-10 grams per dose. In another aspect, the NACA is delivered orally via a mini-tablet, capsule, tablet, effervescent, dual release, mixed release, sachet, powder, or liquid. In another aspect, the NACA is administered prophylactically to prevent age-related macular degeneration, glaucoma, and/or diabetic retinopathy. In another aspect, the dose for administration is between 100 and 900 micrograms per dose. In another aspect, the dose for administration is 100, 150, 150, 300, 350, 400, 500, 600, 700, 750, 800, 900, 1,000, 2,500, 5,000, 7,500, or 10,000 micrograms per dose. In another aspect, the diNACA is administered as an implant one, two, or three times per year.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
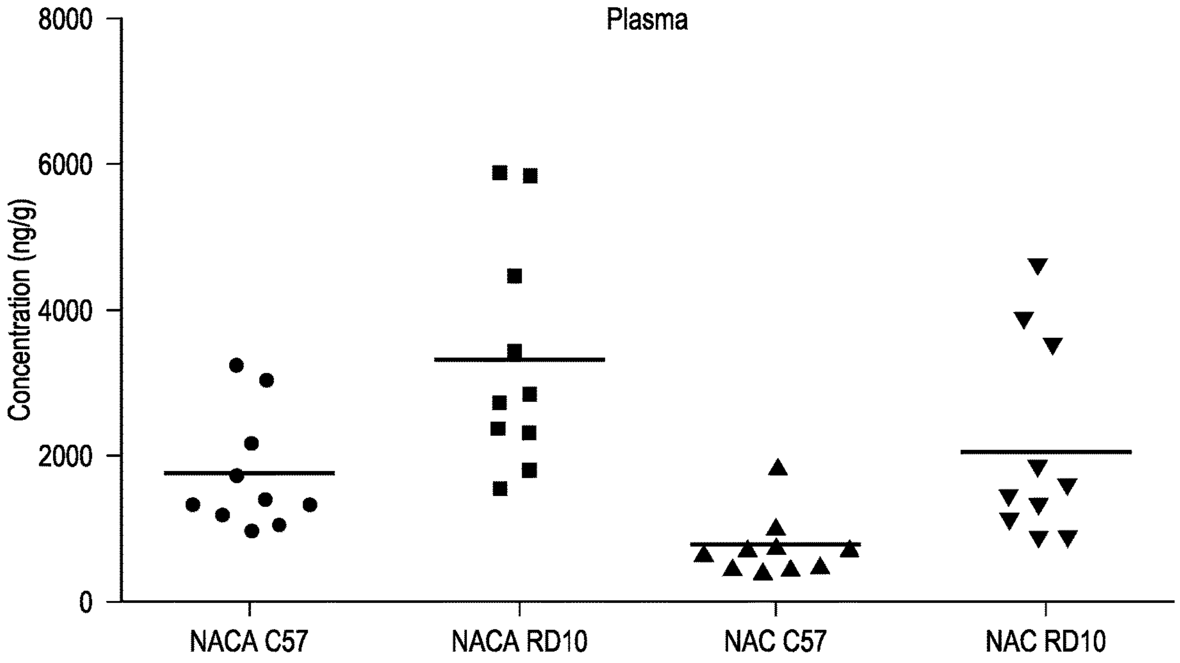
FIG. 1 is a graph that shows the concentration of NACA in plasma.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

Age-related macular degeneration ("AMD") comprises a large group of inherited vision disorders that cause progressive loss of photoreceptor cells of the retina, leading to severe vision impairment and often incurable blindness. The most common form of AMD is a rod-cone dystrophy, in which the first symptom is night blindness, followed by progressive loss in the peripheral visual field in daylight, and eventually leading to blindness after several decades. As a common pathology, rod photoreceptors die early, whereas light-insensitive, morphologically altered cone photoreceptors persist longer.

Diabetic retinopathy (DR), sometimes referred to as diabetic eye disease, in which diabetes mellitus leads to damage to the retina, and is a leading cause of blindness. Typically, DR affects up to 80 percent of diabetic patients. Importantly, the longer a patient has diabetes, the higher the chances of developing diabetic retinopathy. In the United States, diabetic retinopathy accounts for 12% of all new cases of blindness, and is the leading cause of blindness in patients aged 20 to 64.

Glaucoma described several eye diseases that result from damage to the optic nerve leading to loss of vision. Typical symptoms of glaucoma include, e.g., eye pain, blurred vision, mid-dilated pupil, redness of the eye, and nausea. An increase in intraocular pressure is a major risk factor for glaucoma, as are a family history of glaucoma and high blood pressure, however, the etiology of glaucoma is still under investigation.

N-acetyl-L-cysteine amide (NACA), also known as (R)-2-(acetylamino)-3-mercapto-propanamide, N-acetyl-L-cysteinamide, or acetylcysteinamide, has the structure:

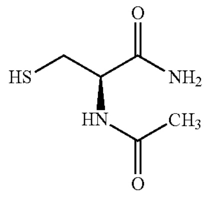

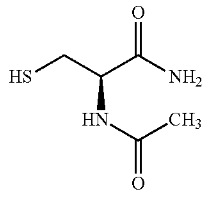

N-acetylcysteine amide (NACA), the amide form of N-acetyl-L-cysteine (NAC), acts as a carrier or prodrug to NAC.

(2R,2R')-3,3'-disulfanediyl bis(2-acetamidopropanamide) (diNACA), has the structure:

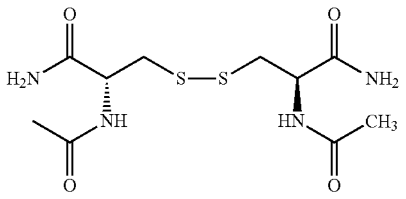

Di-NACA
$C_{10}H_{18}N_4O_4S_2$
Mol Wt: 322.40

(2R,2R')-3,3'-disulfanediyl bis(2-acetamidopropanamide) (diNACA), the dimer form of N-acetyl-L-cysteineamide, acts as a carrier or prodrug to NAC or cysteine. NACA or (2R,2R')-3,3'-disulfanediyl bis(2-acetamidopropanamide) (diNACA) can be used in the treatment of AMD and/or DR.

Currently, there is no approved therapy that stops the evolution of the disease or restores vision. The therapeutic approach is restricted to slowing down the degenerative process by sunlight protection and vitamin A supplementation, treating complications (cataracts and macular edema), and helping patients to cope with the social and psychological impact of blindness. Although the Argis II Retinal Prosthesis System was approved by FDA in 2013 as an implanted device to treat adults with severe vision loss, it only produces the sensation of light, thereby helping patients identify the location or movement of objects and people; the devise is not disease modifying.

Gluthathione (GSH) is a tripeptide, c-L-glutamyl-L-cysteinyl-glycine, found in all mammalian tissues. It has several important functions including detoxification of electrophiles, scavenging ROS<maintaining the thiol status of proteins, and regeneration of the reduced forms of vitamins C and E. GSH is the dominant non-protein thiol in mammalian cells; as such it is essential in maintaining the intracellular redox balance and the essential thiol status of proteins. Also, it is necessary for the function of some antioxidant enzymes such as the glutathione peroxidases.

Intracellular GSH levels are determined by the balance between production and loss. Production results from de novo synthesis and regeneration of GSH from GSSG by GSSG reductase. Generally, there is sufficient capacity in the GSSG reductase system to maintain all intracellular GSH in the reduced state, so little can be gained by ramping up that pathway. The major source of loss of intracellular GSH is transport out of cells. Intracellular GSH levels range from 1-8 mM while extracellular levels are only a few μM; this large concentration gradient essentially precludes transport of GSH into cells and once it is transported out of cells, it is rapidly degraded by γ-glutamyltranspeptidase. Inhibition of GSH transporters could theoretically increase intracellular GSH levels, but is potentially problematic because the transporters are not specific for GSH and their suppression could lead imbalance of other amino acids and peptides. Thus, intracellular GSH levels are modulated primarily by changes in synthesis.

GSH is synthesized in the cytosol of virtually all cells by two ATP-requiring enzymatic steps: L-glutamate+L-cysteine+ATP [→] γ-glutamyl-L-cysteine+ADP+Pi and γ-glutamyl-L-cysteine+L-glycine+ATP [→] GSH+ADP+Pi. The first reaction is rate-limiting and is catalyzed by glutamate cysteine ligase (GCL, EC 6.3.2.2). GCL is composed of a 73Kd heavy catalytic subunit (GCLC) and a 30Kd modifier subunit (GCLM), which are encoded by different genes. GCCL is regulated by nonallosteric competitive inhibition of GSH (Ki=2.3 mM) and by the availability of L-cysteine. The apparent Km of GLC for glutamate is 1.8 mM and intracellular glutamate concentration is roughly 10-fold higher so that glutamate is not limiting, but the Km for cysteine is 0.1-0.3 mM, which approximates its intracellular concentration. The second reaction is catalyzed by GSH synthase (GS, EC 6.3.2.3), which is 118 Kd and composed of two identical subunits. While GS is not felt to be important in regulation of GSH synthesis under normal conditions, it may play a role under stressful conditions because in response to surgical trauma, GSH levels and GS activity were reduced while GCL activity was unchanged. Furthermore, compared to increased expression of GCLC alone, increased expression of both GCLC and GS resulted in higher levels of GSH. In order to maximize the effects of increasing synthetic enzymes, it is necessary to provide increased levels of cysteine. In cultured neurons, 90% of cysteine uptake occurs through by the sodium-dependent excitatory amino acid transporter (EAAT) system. There are five EAATs and cysteine uptake by neurons occurs predominantly by EAAT3 more commonly known as excitatory amino acid carrier-1 (EAAC1). Under normal circumstances most EAAC1 is in the ER and only translocates to the plasma membrane when activated. This translocation is negatively regulated by glutamate transporter associated protein 3-18 (GTRAP3-18) and suppression of GTRAP3-18) increased GSH levels in neurons. Thus, internalization of cysteine provides a roadblock for GSH synthesis, but fortunately it can be bypassed by N-acetylcysteine (NAC) which readily enters cells even in the absence of activated EAAC1. Systemically administered NAC gains access to the CNS, increases GSH levels, and provides benefits in neurodegenerative disorders in which oxidative stress is an important part of the pathogenesis.

All cellular compartments must be protected against oxidative damage, including the cytoplasm, mitochondria, and the nucleus. The present inventors have previously performed gene transfer of enzymes that detoxify reactive oxygen species, but that approach requires the expression of two enzymes in the cytoplasm and two enzymes in mitochondria. In contrast, the present invention provides for protection of all cellular compartments with expression of only two enzymes in the cytosol because GSH is able to diffuse everywhere throughout cells.

NAC is used for the treatment of acetaminophen overdose at a dose of 140 mg/kg as the loading dose, followed by 70 mg/kg every 4 hours for 17 doses, starting 4 hours after the loading dose. In clinical studies, NAC has been administered orally from 400 to 1000 mg once daily and from 200 to 600 mg three times daily. However, following an oral dose of 600 mg in humans, NAC is rapidly absorbed and then rapidly cleared. The plasma half-life of NAC has been reported to be 2.5 hours and no NAC is detectable 10-12 hours after administration. During absorption, NAC is rapidly metabolized to cysteine, which is a direct precursor of glutathione. Based on this evidence, including that NACA is a precursor and/or carrier for NAC, it was expected that NACA would act similarly to NAC in vivo. However, the present inventors demonstrate that NACA acts very differently from NAC for the treatment of AMD.

In accordance with an embodiment, the present invention provides a method for the prevention, amelioration, or treatment of a disease or condition associated with oxidative stress in a subject comprising administration of a therapeutically effective amount of NACA, to increase the amount of glutathione expressed in the tissues of the subject.

As used herein, "active oxygen species" or "reactive oxygen species" are understood as transfer of one or two electrons produces superoxide, an anion with the form O2", or peroxide anions, having the formula O2-" or compounds containing an O—O single bond, for example hydrogen peroxides and lipid peroxides. Such superoxides and peroxides are highly reactive and can cause damage to cellular components including proteins, nucleic acids, and lipids.

As used herein, the term "agent" refers to a therapeutically active compounds or a potentially therapeutic active compound, e.g., an antioxidant. An agent can be a previously known or unknown compound. As used herein, an agent is typically a non-cell based compound, however, an agent can include a biological therapeutic agent, e.g., peptide or nucleic acid therapeutic, e.g., siRNA, shRNA, cytokine, antibody, etc.

As used herein, the terms "amelioration" or "treatment" is understood as meaning to lessen or decrease at least one sign, symptom, indication, or effect of a specific disease or condition. For example, amelioration or treatment of age-related macular degeneration (AMD) can be to reduce, delay, or eliminate one or more signs or symptoms of AMD including, but not limited to, a reduction in night vision, a reduction in overall visual acuity, a reduction in visual field, a reduction in the cone density in one or more quadrants of the retina, thinning of retina, particularly the outer nuclear layer, reduction in a- or b-wave amplitudes on scotopic or photopic electroretinograms (ERGs); or any other clinically acceptable indicators of disease state or progression. Amelioration and treatment can require the administration of more than one dose of an agent, either alone or in conduction with other therapeutic agents and interventions. Amelioration or treatment does not require that the disease or condition be cured.

As used herein, the term "Antioxidant" refers to a molecule for slowing or preventing the oxidation of other molecules. Oxidation is a chemical reaction that transfers electrons from a substance to an oxidizing agent. Such reactions can be promoted by or produce superoxide anions or peroxides. Oxidation reactions can produce free radicals, which start chain reaction that damage cells. Antioxidants terminate these chain reactions by removing free radical intermediates, and inhibit other oxidation reactions by being oxidized themselves. As a result, antioxidants are often reducing agents such as thiols, ascorbic acid or polyphenols. Antioxidants include, but are not limited to, α-tocopherol, ascorbic acid, Mn(III)tetrakis (4-benzoic acid) porphyrin, α-lipoic acid, and n-acetylcysteine.

As used herein, the term "Co-administration" refers to the administration of one or more agents to a subject such that the agents are present and active in the subject at the same time. Co-administration does not require a preparation of an admixture of the agents or simultaneous administration of the agents.

As used herein, the terms "effective amount" or "effective doses" refer to that amount of an agent to product the intended pharmacological, therapeutic or preventive results. The pharmacologically effective amount results in the amelioration of one or more signs or symptoms of a disease or condition or the advancement of a disease or conditions, or causes the regression of the disease or condition. For example, a therapeutically effective amount preferably refers to the amount of a therapeutic agent that decreases vision loss, the loss of overall visual acuity, the loss of visual field, by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more as compared to an untreated control subject over a defined period of time, e.g., 2 weeks, one month, 2 months, 3 months, 6 months, one year, 2 years, 5 years, or longer. More than one dose may be required to provide an effective dose.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such as treatment may be ineffective in a subgroup that can be identified by the expression profile or profiles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as an improvement of symptoms, a cure, a reduction in disease signs or symptoms, extension of life, improvement in quality of life, or other effect generally recognized as positive by medical doctors familiar with treating the particular type of disease or condition.

As used herein, the phrase "oxidative stress related ocular disorders" includes, but is not limited to, age-related macular degeneration, macular degeneration including age related macular degeneration (AMD) both wet and dry, diabetic retinopathy, Lebers optic neuropathy, and optic neuritis.

As used herein, the terms "peroxidases" or "a peroxide metabolizing enzyme" refer to a large family of enzymes that typically catalyze a reaction of the form: ROOR1+ electron donor (2 e-)+2H+→ROH+R1OH For many of these enzymes the optimal substrate is hydrogen peroxide, wherein each R is H, but others are more active with organic hydroperoxides such as lipid peroxides. Peroxidases can contain a heme cofactor in their active sites, or redox-active cysteine or selenocysteine residues.

As used herein, the term phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. For example, pharmaceutically acceptable carriers for administration of cells typically is a carrier acceptable for delivery by injection, and do not include agents such as detergents or other compounds that could damage the cells to be delivered. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations, particularly phosphate buffered saline solutions which are preferred for intraocular delivery.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, intramuscular, intraperotineal, intraocular, intravitreal, subretinal, and/or other routes of parenteral administration. The specific route of administration will depend, inter alia, on the specific cell to be targeted. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect.

As used herein, "plurality" is understood to mean more than one. For example, a plurality refers to at least two, three, four, five, or more.

As used herein, the term a "polypeptide" or "peptide" is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full-length proteins (e.g., fully processed proteins) as well as shorter amino acids sequences (e.g., fragments of naturally occurring proteins or synthetic polypeptide fragments).

As used herein, "prevention" is understood as to limit, reduce the rate or degree of onset, or inhibit the development of at least one sign or symptom of a disease or condition particularly in a subject prone to developing the disease or disorder. For example, a subject having a mutation in a gene, such as the opsin gene, is likely to develop AMD. The age of onset of one or more symptoms of the disease can sometimes be determined by the specific mutation. Prevention can include the delay of onset of one or more signs or symptoms of AMD and need not be prevention of appearance of at least one sign or symptom of the disease throughout the lifetime of the subject. Prevention can require the administration of more than one does of an agent or therapeutic.

As used herein, the term "small molecule" refers to a compound, typically an organic compound, having a molecular weight of no more than about 1500 Da, 1000 Da, 750 Da, or 500 Da. In an embodiment, a small molecule does not include a polypeptide or nucleic acid including only natural amino acids and/or nucleotides.

As used herein, the term "subject" refers to living organisms, in particular, humans. In certain embodiments, the living organism is an animal, in certain preferred embodiments, the subject is a mammal, in certain embodiments, the subject is a domesticated mammal or a primate including a non-human primate. Examples of subject include humans, monkeys, dogs, cats, mice, rates, cows, horses, goats, and sheep. A human subject may also be referred to as a subject or patient.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition or syndrome. Methods for identification of subjects suffering from or suspected of suffering from conditions such as AMD and age-related macular degeneration (AMD) is within the ability of those in the art. Subjects suffering from, and suspected of suffering from, a specific disease, condition, or syndrome are not necessarily two distinct groups.

As used herein, "superoxide dismutase" is understood as an enzyme that dismutation of superoxide into oxygen and hydrogen peroxide. Examples include, but are not limited to SOD1, SOD2, and SOD3. Sod1 and SOD3 are two isoforms of Cu—Zn-containing superoxide dismutase enzymes exists in mammals. Cu—Zn-SOD or SOD1, is found in the intracellular space, and extracellular SOD (ECSOD or SOD3) predominantly is found in the extracellular matrix of most tissues.

As used herein, the term "therapeutically effective amount," refers to an amount of an agent which is effective, upon single or multiple does administration to the cell or subject, in prolonging the survivability of the patient with such a disorder, reducing one or more signs or symptoms of the disorder, preventing or delaying and the like beyond that expected in the absence of such treatment.

An agent or other therapeutic intervention can be administered to a subject, either alone or in combination with one or more additional therapeutic agents or interventions, as a pharmaceutical composition in mixture with conventional excipient, e.g., pharmaceutically acceptable carrier, or therapeutic treatments.

The pharmaceutical agents may be conveniently administered in unit dosage form and may be prepared by any of the methods well known in the pharmaceutical arts, e.g., as described in Remington's Pharmaceutical Sciences (Mack Pub. Co., Easton, PA, 1985). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain agents.

The present invention is directed to the use of NACA to treat AMD. In one embodiment, the present invention includes a method for the treatment of age-related macular degeneration in a human that comprises administering to the human therapeutically effective amount of NACA. In some embodiments, the NACA is provided in or with a pharmaceutically acceptable carrier. In other embodiments, the NACA is administered intraocularly, subretinally, intravitreally, orally, intravenously, intramuscularly, topically, sublingually, or rectally.

Animals and Treatments. Mice were treated in accordance with the recommendations of the Association for Research in Vision and Ophthalmology. Litters of homozygous rd10/rd10 mice (B6.CXB1-Pde6brd10/J) and wild type C57/BL6 mice (The Jackson Laboratory, Bar Harbor, ME) were used for these studies.

Starting on post-natal day 28 (P28), animals were given normal drinking water (n=10 for each strain) or water containing 20 mg/ml NACA (n=10 for each strain).

Analysis of NACA and NAC. Upon sacrifice of the mice on P35, retina, aqueous, vitreous and plasma were collected, weighed, and stabilized as quickly as possible and stored at −80° C. prior to shipment to AIT Bioscience, LLC (Indianapolis, IN). The bioanalytical method (BAM.0445.01) for the quantitation of total NAC NACA in $K_2EDTA$ was based on derivatization, protein precipitation extraction, and LC-MS/MS instrumental analysis. Any disulfides were reduced to free thiols and subsequently reacted with 2-chloro-1-methylpyridinium iodide (CMPI) to form stable thioethers. The thioether derivatives were detected by LC-MS/MS. Stable label isotope internal standards were used. The method covered a concentration range from 50.0 to 50,000 ng/mL. The thiol moiety of NAC, NACA, and their respective internal standards oxidizes quickly in plasma through formation of disulfides. In order to determine total NAC and total NACA levels in plasma, tris(2-carboxyethyl)phosphine (TCEP) is added during the extraction to reduce disulfide bonds. Ammonium bicarbonate is added to control sample pH near neutral, as TCEP will otherwise acidify the aliquoted samples and hinder derivatization. The free analyte is then derivatized to a stable thioether using 2-chloro-1-methylpyridinium iodide (CMPI). N-acetyl-L-cysteine is used as the reference standard. The assay would not discern the enantiomer, N-acetyl-D-cysteine, if present. A sample volume of 25.0 μL was aliquotted into a 1.2 mL 96-well plate to which was added, in sequence, 25.0 μL internal standard solution (1000 ng/mL NAC-D3 and 1000 ng/mL NACA-D3 in water), 50.0 μL of ammonium bicarbonate (100 mM), 5.0 μL CMPI (60 mM in water), and 5.0 μL of TCEP (60 mM in water). Samples were allowed to react for 30 minutes. To precipitate proteins, 500 μL of acetonitrile was then added to all samples. The plate was covered and the mixtures were shaken and centrifuged. A 50.0 μL aliquot of the supernatant was transferred from each well to a clean plate containing 400 μL of water-acetonitrile (25-75) in each well, and mixed well prior to LC-MS injection.

FIG. 1 shows the thioether derivatives of NAC and NACA for LCMS analyses.

Samples were analyzed on a Waters Acquity liquid chromatograph interfaced with a Thermo Scientific TSQ Vantage triple quadrupole mass spectrometer with ESI ionization. Each extracted sample was injected (5.0 μL) onto a Waters BEH HILIC column (2.1×100 mm; 1.7 μm) equilibrated at 35° C. Mobile Phase A was ammonium formate (25 mM, pH 3.8). Mobile Phase B was acetonitrile. The LC gradient is tabled below:

| Time (min) | Flow Rate (mL/min) | % MP A | % MP B |
|---|---|---|---|
| 0.00 | 0.500 | 25.0 | 75.0 |
| 2.30 | 0.500 | 25.0 | 75.0 |

The retention time, mass transition and precursor charge state for each compound are as follows. The masses below are for the CMPI thioether derivatives.

| Compound | Expected Retention Time (min) | Precursor Mass/Charge (m/z) | Product Observed Mass/Charge (m/z) | Charge State of Precursor Ion |
|---|---|---|---|---|
| N-Acetyl-L-Cysteine (NAC) | 1.90 | 255.080 | 126.16 | +1 |
| N-Acetylcysteine amide (NACA) | 1.25 | 254.096 | 126.16 | +1 |
| N-Acetyl-L-Cys-$D_3$ | 1.90 | 258.099 | 126.15 | +1 |
| N-Acetyl-L-Cysteine-$D_3$ | 1.25 | 257.115 | 126.15 | +1 |

Peak area ratios from the calibration standard responses were regressed using a (1/concentration$^2$) linear fit for N-Acetyl-L-Cysteine and N-Acetylcysteine amide.

NACA Preclinical Study Proposal for Experiment #1: Evaluation of Retinal Penetration of NACA, as amended July 2017 (Changed Initiation of treatment from P14 to P21 and changed termination point from P21 changed to P35 to match the time points in companion studies.). The research was performed in 3 discrete experiments.

Evaluation of Retinal Penetration of NACA. To determine retinal levels of NACA/NAC after administration of 20 mg/mL NACA in drinking water for 7 days. This experiment will provide rapid confirmation that NACA and/or NAC penetrate the retina following oral administration. This experiment will also evaluate if the breakdown in the blood-retinal barrier in RP affects the levels of NACA in the retina by comparing animals with RP to wild type mice.

Rd10 and C57BL/6 wild type mice will begin treatment at P28 and at P35 mice will be euthanized and plasma, vitreous and retina samples will be sent to AITB for determination of NAC and NACA levels. Experimental groups: (n=10/group). The research was performed in 3 discrete experiments:

1. Rd10 NACA 20 mg/mL in drinking water measurements at P35;
2. Rd10 with no addition to drinking water measurements at P35;
3. C57/BL6 NACA 20 mg/mL in drinking water measurements at P35;
4. C57/BL6 with no addition to drinking water measurements at P35.

All levels of NACA and NAC were below the limit of quantification of the assay (BLQ) for mice which did not receive NACA in the drinking water. Nearly all measurements of NACA and NAC in aqueous, vitreous and retina were also BLQ and are not discussed.

The mean NACA levels in plasma for animals treated with 20 mg/ml in drinking water were greater than the NAC levels in both strains of mice (N=10 for each strain). The mean NACA levels and NAC levels were greater in rd10 mice than in the wild type. (FIG. 1).

Figure 2:
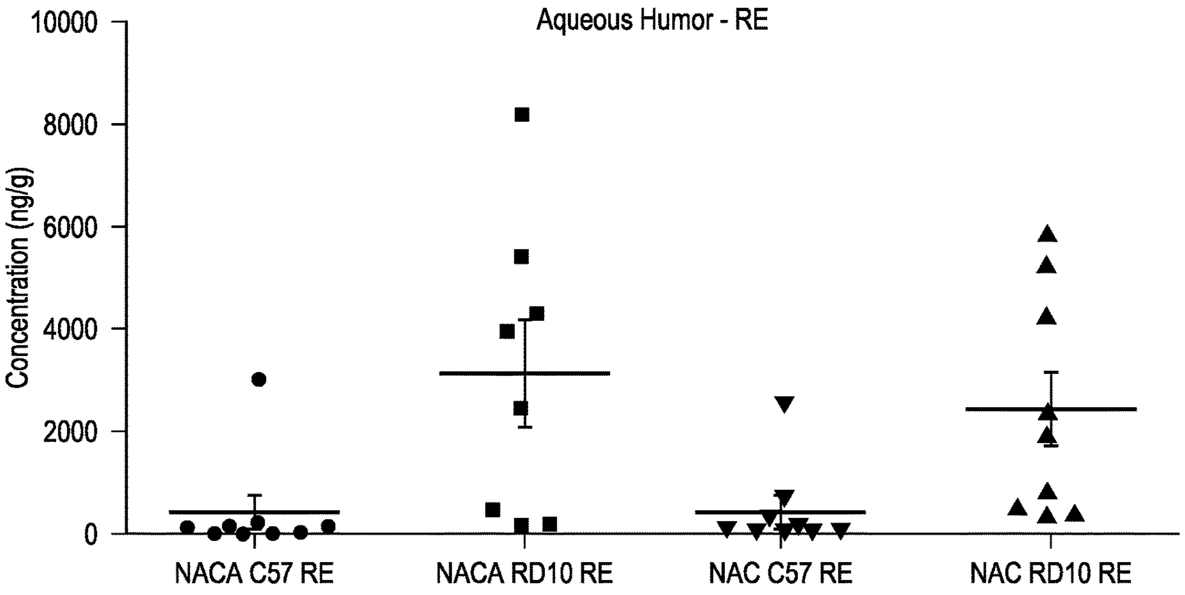
FIG. 2 is a graph that shows the concentration of NACA in the aqueous humor.
Figure 3:
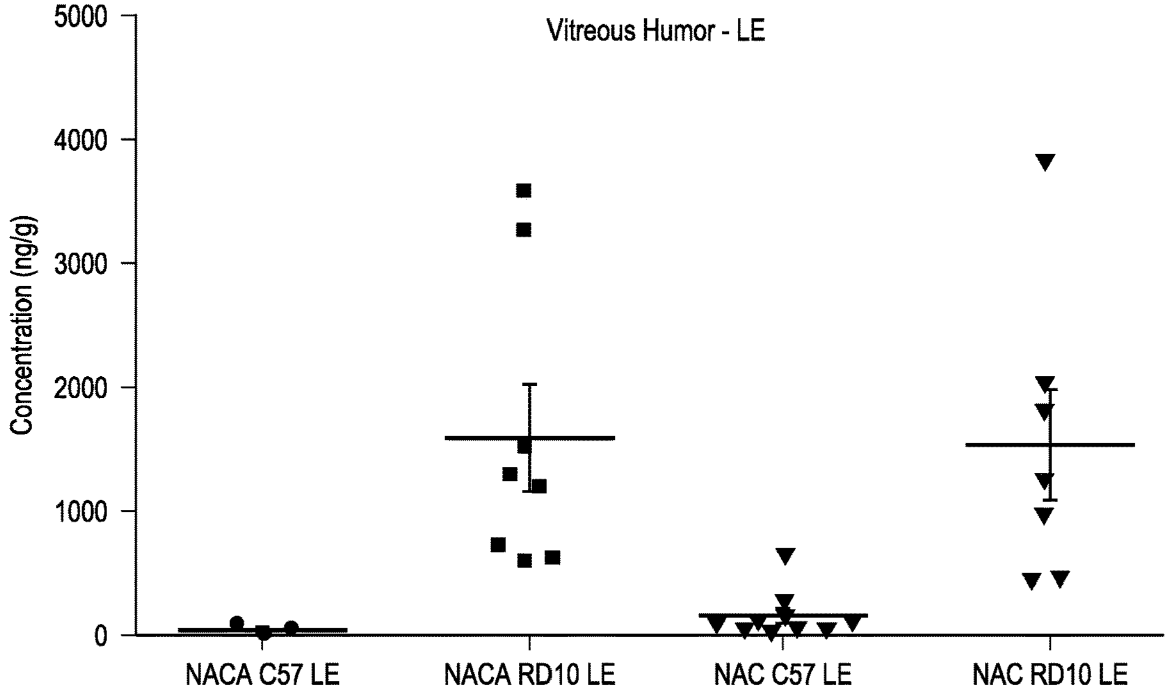
FIG. 3 is a graph that shows the concentration of NACA in the vitreous humor.
Figure 4:
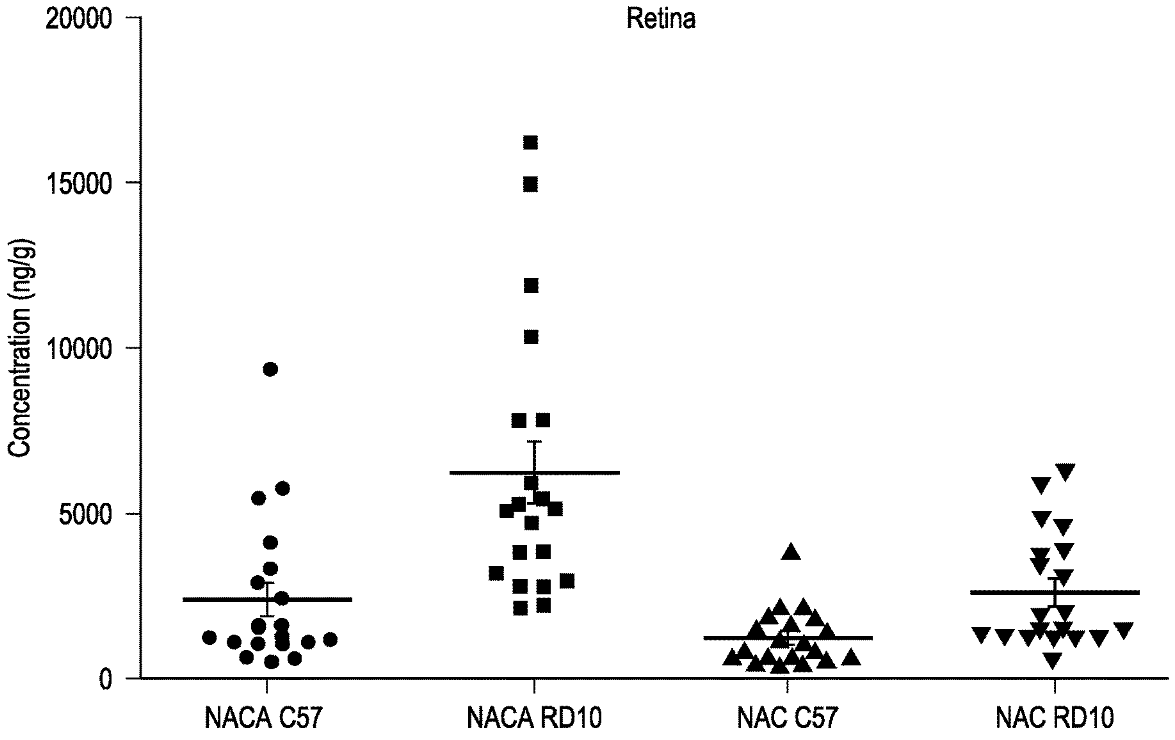
FIG. 4 is a graph that shows the concentration of NACA in the retina.
Figure 5:
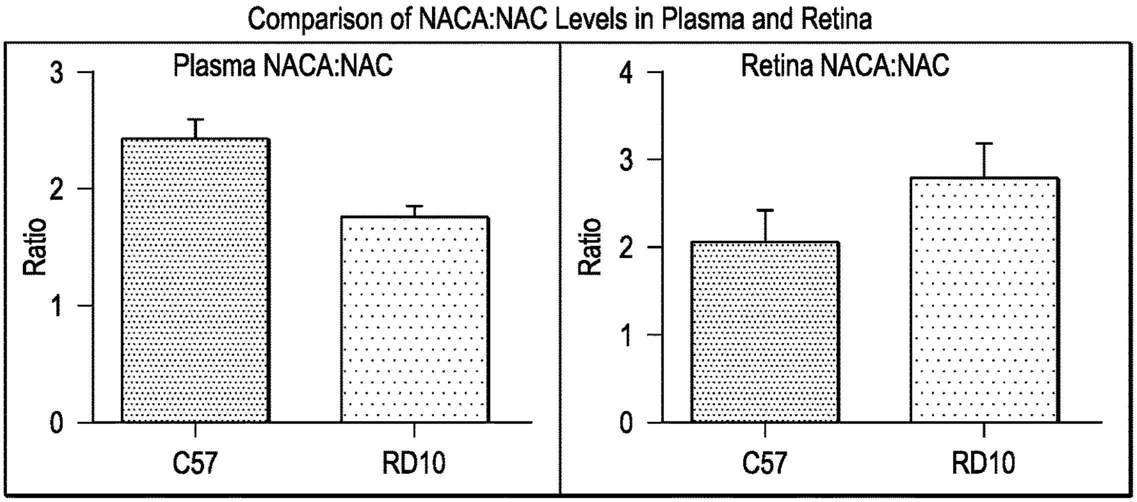
FIG. 5 is a graph that shows a comparison of NACA:NAC Levels in the plasma and retina.
Figure 6:
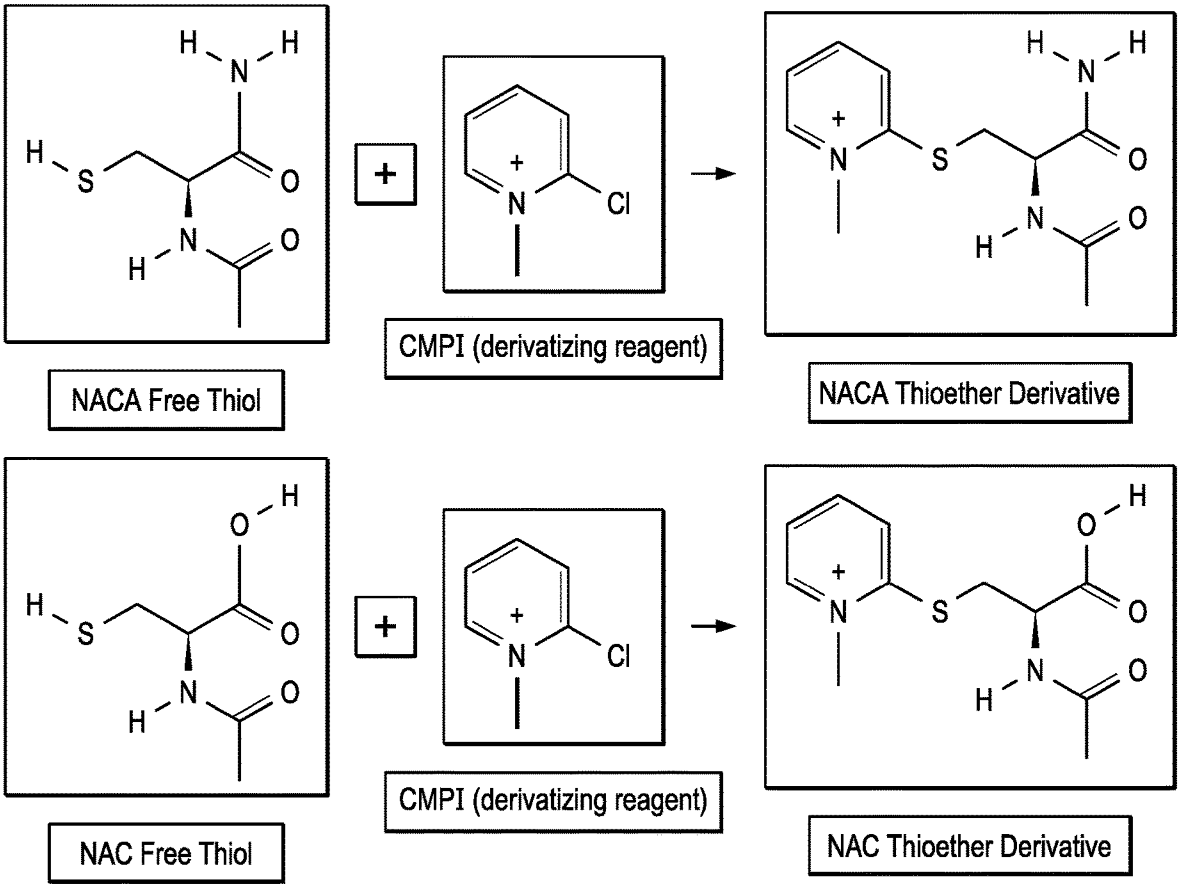
FIG. 6 shows the thioether derivatives of NAC and NACA for LCMS analyses.

The mean NACA and NAC levels in aqueous humor were lower than in plasma. The mean concentration of NACA in the aqueous humor (N=8 eyes for rd10, N=10 for C57/B16) was also higher in rd10 mice than wild type. (FIG. 2). A similar pattern was observed for the vitreous humor (N=7 or 8 eyes for rd10, N=10 eyes for C57/B16). (FIG. 3). In the retina, NACA and NAC were measurable in all animals treated with NACA (N=20 eyes for each strain). The mean levels of NACA and NAC were higher than those observed in plasma (FIG. 4). The ratio of NACA:NAC in the retina indicates that NACA penetrated retina to a greater extent in rd10 mice than in C57/B16 mice (FIG. 5). FIG. 6 shows the thioether derivatives of NAC and NACA for LCMS analyses.

The data from this experiment demonstrate that NACA levels are measurable in the target tissue (the retina) following oral administration of 20 mg/mL in drinking water. It is estimated that mice consume 3-4 mL of water/day, leading to an estimated dose of NACA of 60-80 mg/day. These doses resulted in mean retina levels of approximately 6.5 μg/g in rd10 mice and 2.4 μg/g in wild type mice. It is notable that the ratio of NACA:NAC is greater in the retina of rd10 mice than in C57/B16 mice, suggesting that the disruption of the blood-retinal barrier in RP allows better penetration of NACA.

It will be appreciated that the actual preferred amounts of active compounds used in a given therapy will vary according to e.g., the specific compound being utilized, the particular composition formulated, the mode of administration and characteristics of the subject, e.g., the species, sex, weight, general health and age of the subject. Optimal administration rates for a given protocol of administration can be readily ascertained by those skilled in the art using conventional dosage determination tests conducted with regard to the forgoing guidelines.

Ranges provided herein are understood to be shorthand for all of the values within the range.

As used herein, the embodiments of this invention are defined to include pharmaceutically acceptable derivatives thereof. A "pharmaceutically acceptable derivative" means any pharmaceutically salt, ester, salt of an ester, or other derivative of a compound of this invention which, upon administration to a recipient, is capable of providing (directly or indirectly) a compound of this invention. Particularly favored derivatives are those that increase the bioavailability of the compounds of this invention when such compounds are administered to a mammal (e.g., by allowing an orally administered compound to be more readily absorbed into the blood, to increase serum stability or decrease clearance rate of the compound) or which enhance delivery of the parent compound to a biological compartment (e.g., the brain or lymphatic system) relative to the parent species. Derivatives include derivatives where a group which enhances aqueous solubility or active transport through the gut membrane is appended to the structure of formulae described herein.

The embodiments of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-napthalenesulfonate, nicotinate, nitrate, palmoate, phosphate, picrate, pivalate, propionate, salicylate, succinate, sulfate, tartrate, tosylate, and undeconaoate. Salts derived from appropriate bases include alkali metal (e.g., sodium), alkaline earth metal (e.g., magnesium), ammonium and N-(alkyl)4+ salts. This invention also envisions the quaternization of any basic nitrogen-containing groups of the compounds disclosed herein. Water or oil-soluble or dispersible products may be obtained by such quaternization.

The embodiments of the invention can, for example, be administered by injection, intraocularly, intravitreally, subretinal, intravenously, intraarterially, subdermally, intramuscularly, or subcutaneously; or orally, buccally, nasally, transmucosally, directly to a diseased organ by catheter, topically, or in an ophthalmic preparation, with a dosage ranging from about 0.001 to about 100 mg/kg of body weight, or according to the requirements of the particular drug and more preferably from 0.5, 1, 2, 3, 4, 5, 6, 7, 8, 9, 10, 15, 20, 25, 30, 40, 50, 60, 70, 75, 80, 90, 100, 110, 120, 125, 130, 140 or 150 mg/kg of body weight. It is understood that when a compound is delivered directly to the eye, considerations such as body weight have less bearing on the dose. In another aspect, the dose for administration is between 100 and 900 micrograms per dose. In another aspect, the dose for administration is 100, 150, 150, 300, 350, 400, 500, 600, 700, 750, 800, 900, 1,000, 2,500, 5,000, 7,500, or 10,000 micrograms per dose. In another aspect, the diNACA is administered as an implant one, two, or three times per year.

Frequency of dosing will depend on the agent administered, the progression of the disease or condition in the subject, and other considerations known to those of skill in the art. For example, pharmacokinetic and pharmacodynamics considerations for compositions delivered to the eye, or even compartments within the eye, are different, e.g., clearance in the subretinal space is very low. Therefore, dosing can be as infrequent as once a month, once every three months, once every six months, once a year, once every five years, or less. If systemic administration of antioxidants is to be performed in conjunction with administration of expression constructs to the subretinal space, it is expected that the dosing frequency of the antioxidant will be higher than the expression construct, e.g., one or more times daily, one or more times weekly.

Dosing may be determined in conjunction with monitoring of one or more signs or symptoms of the disease, e.g., visual acuity, visual field, night visions, etc. The amount of active ingredient that may be combined with the carrier materials to produce a single dosage form will vary depending upon the host treated and the particular mode of administration. A typical preparation will contain from about 1% to about 95% active compound (w/w). Alternatively, such preparations contain from about 20% to about 80% active compound. Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity ad course of the disease, condition or symptoms, the patient's disposition to the disease, condition or symptoms and the judgment of the treating physician.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, TWEEN® 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as TWEENs® or SPAN® and/or other similar emulsifying agents or bioavailability enhancers which are commonly used in the manufacture of pharmaceutically acceptable solid, liquid, or other dosage forms may also be used for the purposes of formulation.

In one or more embodiments, NACA is administered in daily doses of about 0.5, 1, 2, 3, 4, 5, 6, 7, 8, 9, 10, 15, 20, 25, 30, 40, 50, 60, 70, 75, 80, 90, 100, 110, 120, 125, 130, 140 or 150 mg/Kg. In other embodiments, NACA is administered two or three times daily. In another aspect, NACA is administered with a second active agent selected from ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like. In another aspect, the dose for administration is between 100 and 900 micrograms per dose. In another aspect, the dose for administration is 100, 150, 150, 300, 350, 400, 500, 600, 700, 750, 800, 900, 1,000, 2,500, 5,000, 7,500, or 10,000 micrograms per dose. In another aspect, the diNACA is administered as an implant one, two, or three times per year.

In some embodiments, the dose of NACA for administration is, 100, 150, 150, 300, 333, 400, 500, 600, 700, 750, 800, 900, 1,000, 2,500, 5,000, 7,500, or 10,000 mg per dose. In another aspect, the dose for administration is 0.1-0.25, 0.1-0.4, 0.35-0.5, 0.5-1, 102, 1-3, 1-4, 1-5, 1-2.5, 2.5-3.5, 4-6, 5-8, 6-9, 7-10 grams per dose. In another aspect, the NACA is delivered orally via a mini-tablet, capsule, tablet, effervescent, dual release, mixed release, sachet, powder, or liquid. In another aspect, the NACA is administered prophylactically to prevent AMD. In another aspect, the dose for administration is between 100 and 900 micrograms per dose. In another aspect, the dose for administration is 100, 150, 150, 300, 350, 400, 500, 600, 700, 750, 800, 900, 1,000, 2,500, 5,000, 7,500, or 10,000 micrograms per dose. In another aspect, the diNACA is administered as an implant one, two, or three times per year.

In another embodiment, the present invention includes a method for the treatment of AMD comprising: identifying a human in need of treatment for age-related macular degeneration; and administering to the human a therapeutically effective amount of NACA sufficient to treat AMD. It will be understood that, as with the other embodiments defined above, NACA is administered in daily doses of about 0.5, 1, 2, 3, 4, 5, 6, 7, 8, 9, 10, 15, 20, 25, 30, 40, 50, 60, 70, 75, 80, 90, 100, 110, 120, 125, 130, 140 or 150 mg/Kg. In another aspect, NACA is administered two or three times daily. In another aspect, NACA is administered with a second active agent as disclosed above. In another aspect, the dose for administration is between 100 and 900 micrograms per dose. In another. aspect, the dose for administration is 100, 150, 150, 300, 350, 400, 500, 600, 700, 750, 800, 900, 1,000, 2,500, 5,000, 7,500, or 10,000 micrograms per dose. In another aspect, the diNACA is administered as an implant one, two, or three times per year.

In another aspect, the dose of NACA for administration is 100, 150, 150, 300, 333, 400, 500, 600, 700, 750, 800, 900, 1,000, 2,500, 5,000, 7,500, or 10,000 mg per dose. In another aspect, the dose for administration is 0.1-0.25, 0.1-0.4, 0.35-0.5, 0.5-1, 102, 1-3, 1-4, 1-5, 1-2.5, 2.5-3.5, 4-6, 5-8, 6-9, 7-10 grams per dose. In another aspect, the NACA is delivered orally via a mini-tablet, capsule, tablet, effervescent, dual release, mixed release, sachet, powder, or liquid. In another aspect, NACA is administered prophylactically to prevent AMD. In another aspect, the dose for administration is between 100 and 900 micrograms per dose. In another aspect, the dose for administration is 100, 150, 150, 300, 350, 400, 500, 600, 700, 750, 800, 900, 1,000, 2,500, 5,000, 7,500, or 10,000 micrograms per dose. In another aspect, the diNACA is administered as an implant one, two, or three times per year.

As used herein, "susceptible to" or "prone to" or "predisposed to" a specific disease or condition or the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200% or more.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" issued to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refer condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organization cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims. laucoma, or diabetic retinopathy.

What is claimed is:

1. A method for treatment of age-related macular degeneration, glaucoma, or diabetic retinopathy in a human subject that comprises:

administering to the human patient a therapeutically effective amount of (2R,2R')-3,3'-disulfanediyl bis(2-acetamidopropanamide) (diNACA), N-Acetylcysteine amide (NACA), or both, in or with a pharmaceutically acceptable carrier wherein a concentration of NACA or diNACA in the retina is greater than a plasma concentration after 4 hours.

2. The method of claim 1, wherein the diNACA, NACA, or both is administered orally, intravenously, intramuscularly, enterally, intraocularly, subretinally, intravitreally, topically (including topical ocular), sublingually, or rectally.

3. The method of claim 1, wherein the diNACA, NACA, or both is at least one of: administered in daily doses of about 0.5, 1, 2, 3, 4, 5, 6, 7, 8, 9, 10, 15, 20, 25, 30, 40, 50, 60, 70, 75, 80, 90, 100, 110, 120, 125, 130, 140 or 150 mg/Kg; administered two or three times daily; or administered with a second active agent selected from at least one of ascorbic acid, cysteine hydrochloride, sodium bisulfate, sodium metabisulfite, sodium sulfite, ascorbyl palmitate, butylated hydroxyanisole (BHA), butylated hydroxytoluene (BHT), lecithin, propyl gallate, α-tocopherol, citric acid, ethylenediamine tetraacetic acid (EDTA), sorbitol, tartaric acid, or phosphoric acid.

4. The method of claim 1, wherein a dose for administration is 100, 150, 150, 300, 333, 400, 500, 600, 700, 750, 800, 900, 1,000, 2,500, 5,000, 7,500, or 10,000 mg per dose.

5. The method of claim 1, wherein the diNACA, NACA, or both is delivered orally via a mini-tablet, capsule, tablet, effervescent, dual release, mixed release, sachet, powder, or liquid.

6. The method of claim 1, wherein the diNACA, NACA, or both is administered prophylactically to prevent age-related macular degeneration, glaucoma, or diabetic retinopathy.

7. The method of claim 1, wherein the therapeutically effective is the amount of a therapeutic agent that decreases at least one of a loss of night vision, a loss of overall visual acuity, or a loss of visual field, by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more as compared to an untreated control subject over a defined period of time, selected from at least one of 2 weeks, one month, 2 months, 3 months, 6 months, one year, 2 years, or 5 years.

8. The method of claim 1, wherein a blood-retinal barrier is compromised artificially or mechanically with an ultrasound, laser, or a penetrator, or chemically, wherein the blood-retinal barrier is compromised chemically with at least one of a microbubble, a toxin, TNF-α, cryotherapy, monomeric C-reactive Protein (mCRP), HIV-1 gp120 glycoprotein, or a *Toxoplasma gondii* toxin, and wherein the blood-retinal barrier is reversibly compromised.

9. The method of claim 1, wherein a dose for administration is between 100 and 900 micrograms per dose.

10. The method of claim 1, wherein a dose for administration is 100, 150, 150, 300, 350, 400, 500, 600, 700, 750, 800, 900, 1,000, 2,500, 5,000, 7,500, or 10,000 micrograms per dose.

11. The method of claim 1, wherein the diNACA, NACA, or both is administered as an implant one, two or three times per year.

* * * * *